(12) United States Patent
Randolph et al.

(10) Patent No.: US 6,423,880 B1
(45) Date of Patent: Jul. 23, 2002

(54) ISOPENTANE DISPROPORTIONATION

(75) Inventors: Bruce B. Randolph, Bartlesville, OK (US); Kenneth C. Hoover, New Hartford, NY (US); Martyn E. Pfile, Bartlesville, OK (US)

(73) Assignee: Phillips Petroleum Company, Bartlesville, OK (US)

( * ) Notice: Subject to any disclaimer, the term of this patent is extended or adjusted under 35 U.S.C. 154(b) by 0 days.

(21) Appl. No.: 09/596,456

(22) Filed: Jun. 19, 2000

(51) Int. Cl.[7] .................................................. C07C 6/08
(52) U.S. Cl. ........................ 585/708; 585/706; 585/310
(58) Field of Search ................................. 585/708, 702, 585/706, 310

(56) References Cited

U.S. PATENT DOCUMENTS

| 5,489,727 A | 2/1996 | Randolph et al. ........... 585/702 |
| 5,900,522 A | 5/1999 | Hommeltoft ................. 585/708 |

*Primary Examiner*—Walter D. Griffin
(74) *Attorney, Agent, or Firm*—Jeffrey R. Anderson

(57) ABSTRACT

A novel i-pentane disproportionation process is provided and includes contacting i-pentane with an acidic disproportionation catalyst in the presence of a lower paraffin co-feed and, optionally, in the presence of an initiator.

30 Claims, 1 Drawing Sheet

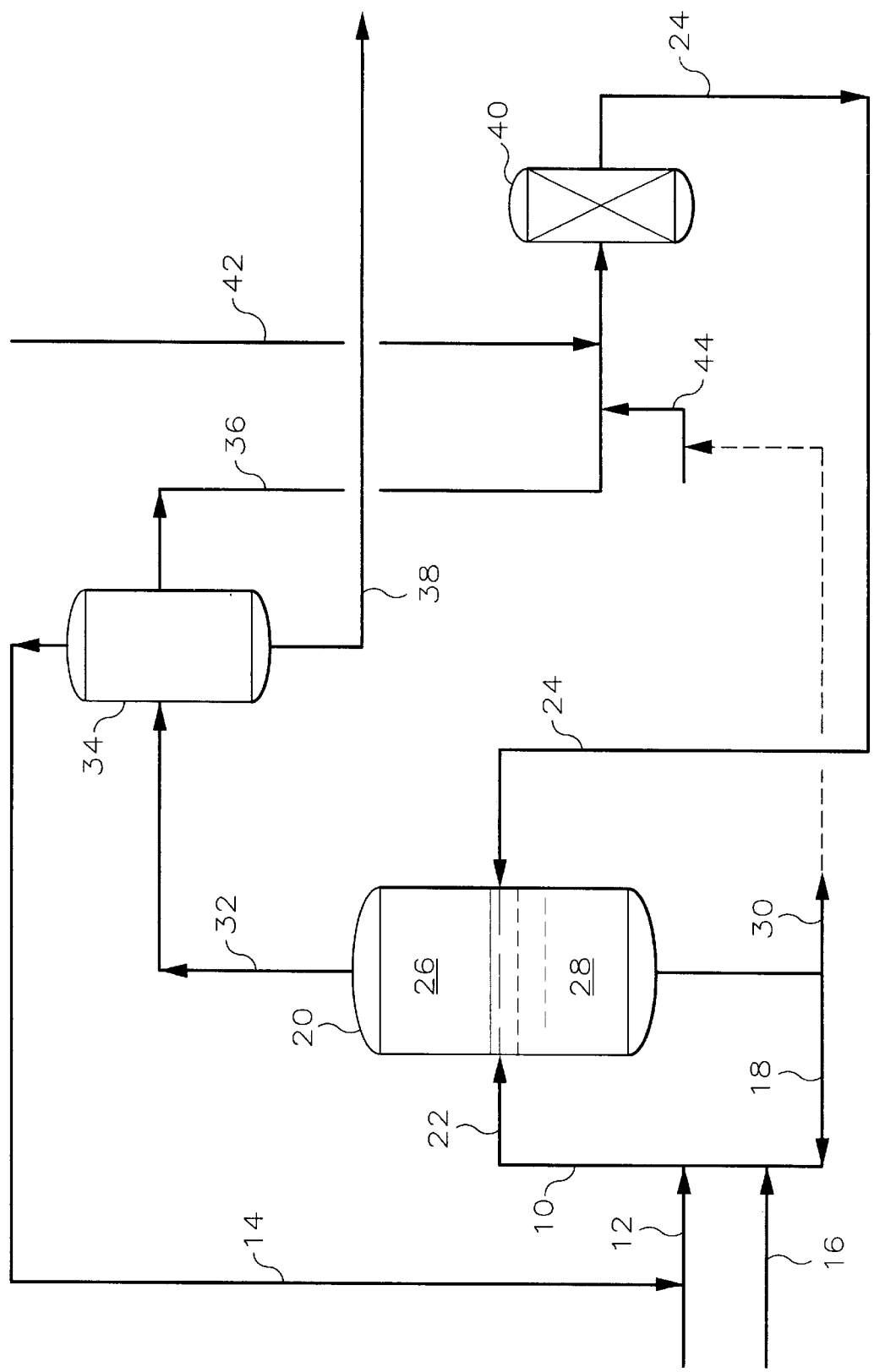

ISOPENTANE DISPROPORTIONATION

This invention relates to the production of i-butane and $C_6+$ isoparaffin containing products. More particularly, this invention relates to the production of i-butane and $C_6+$ isoparaffins by disproportionating i-pentane in the presence of an acidic catalyst, and a lower paraffin co-feed.

BACKGROUND OF THE INVENTION

The disproportionation of i-pentane to i-butane and $C_6+$ isoparaffins is well known in the art and has been described in U.S. Pat. No. 5,489,727. This process has gained importance due to governmental regulations requiring reduction of the amount of volatile $C_4$ and $C_5$ alkanes present in gasoline. Also, there is an incentive to convert isopentanes to higher isoparaffins, such as, isohexane which is a lower vapor pressure motor fuel component, and to isobutane which is a feedstock for alkylation with olefins to high octane alkylate and also for the production of MTBE.

Therefore, development of an improved process for disproportionating i-pentane would be a significant contribution to the art.

Furthermore, it has been unexpectedly discovered that the presence of a lower paraffin co-feed in an i-pentane disproportionation feed enhances the conversion of i-pentane.

SUMMARY OF THE INVENTION

It is an object of the present invention to provide an improved process for disproportionating i-pentane.

It is another object of the present invention to provide an improved process for disproportionating i-pentane to i-butane and $C_6+$ isoparaffins by adding a lower paraffin to the feed mixture for contact with a disproportionation catalyst.

It is yet another object of the present invention to provide a process for increasing the conversion of i-pentane in an i-pentane disproportionation process by adding a lower paraffin to the i-pentane feed.

In accordance with the present invention, a process for disproportionating isopentane has been discovered comprising contacting a hydrocarbon feed comprising at least one i-pentane and a lower paraffin with an acidic disproportionation catalyst in a reaction zone under disproportionation reaction conditions.

Other objects and advantages will become apparent from the detailed description and the appended claims.

BRIEF DESCRIPTION OF THE DRAWING

The FIGURE is a schematic flow diagram presenting an embodiment of the present invention.

DETAILED DESCRIPTION OF THE INVENTION

The process of the present invention comprises, consists of, or consists essentially of contacting a hydrocarbon feed with an acidic disproportionation catalyst in a reaction zone under disproportionation reaction conditions and, optionally, in the presence of an initiator.

The hydrocarbon feed can be any hydrocarbon-containing feed which comprises, consists of, or consists essentially of at least one isopentane (such as, 2-methylbutane, 2,2-dimethylpropane, or mixtures thereof) and a lower paraffin preferably selected from the group consisting of propane, n-butane, and combinations thereof. Generally, the feed contains in the range of from about 1 wt. % to about 99 wt. % isopentane(s). The hydrocarbon feed also preferably contains/comprises less than 6 wt. %, more preferably less than 5 wt. %, and most preferably less than 4 wt. % water. The mole ratio of isopentane to lower paraffin in the hydrocarbon feed is in the range of from about 0.01 to about 80; preferably from about 0.1 to about 10; and most preferably from 1 to 5.

The preferred lower paraffin in the hydrocarbon feed is n-butane.

The hydrocarbon feed can be a n-butane/i-pentane mixture stream obtained from an alkylation process, or obtained from the processing of natural gas liquids, or an olefin/paraffin stream obtained from a thermal or catalytic cracking process.

The catalyst useful in the alkylation process can comprise, consist of, or consist essentially of an acid selected from the group consisting of hydrofluoric acid, sulfuric acid, halides of the Group III metals (and combinations thereof), halogenated zeolites, a polyfluoroalkane sulfonic acid, regenerable solid acids such as halogenated alumina containing noble metals (such as gold, silver, platinum, palladium, iridium, rhenium, mercury, ruthenium, and osmium), and combinations of any two or more thereof. The polyfluoroalkane moiety contains in the range of from 1 to 20 carbon atoms.

The initiator useful in the present invention can be any compound capable of initiating a hydrogen transfer reaction, and preferably, is a compound selected from the group consisting of a haloalkane, a branched paraffin, at least one olefin, and combinations of any two or more thereof. The haloalkane preferably comprises a compound selected from the group consisting of fluoropropane, fluorobutanes, fluoropentanes, and combinations of any two or more thereof. The branched paraffin preferably comprises a multi-branched paraffin having in the range of from 4 to 20 carbon atoms per molecule, and combinations of any two or more thereof. The at least one olefin preferably comprises an olefin having in the range of from 3 to 20 carbon atoms per molecule, and combinations of any two or more thereof. The most preferred olefin for use as the initiator comprises an olefin selected from the group consisting of propylene, a butylene, a pentene, and combinations of any two or more thereof.

When present, the concentration of the initiator in the reaction zone, based on the combined weight of the hydrocarbon feed and initiator in the reaction zone, is greater than about 0.01 wt. %, preferably greater than about 0.1 wt. % and most preferably from 0.5 wt. % to 40 wt. %.

The acidic disproportionation catalyst useful in the present invention can be any catalyst suitable for catalyzing carbocation reactions between secondary and tertiary carbenium ions. The acidic disproportionation catalyst preferably comprises, consists of, or consists essentially of an acid selected from the group consisting of sulfuric acid, halides of the Group III metals (and combinations thereof), halogenated zeolites, hydrofluoric acid, a polyfluoroalkane sulfonic acid, wherein the polyfluoroalkane moiety contains in the range of from 1 to 20 carbon atoms, regenerable solid acids such as halogenated alumina containing noble metals (such as gold, silver, platinum, palladium, indium, rhenium, mercury, ruthenium, and osmium), and combinations of any two or more thereof. The most preferred acidic disproportionation catalyst is hydrofluoric acid.

The disproportionation reaction conditions can be any conditions suitable for disproportionating i-pentane to i-butane and $C_6+$ isoparaffins. Preferably, the disproportionation reaction conditions include a temperature in the range of from about 75° F. to about 375° F., more preferably from about 100° F. to about 300° F., and most preferably from 125° F. to 215° F. Also, the disproportionation reaction conditions include a contact time of the hydrocarbon feed with the acidic disproportionation catalyst in the range of from about 30 seconds to about 2 hours, preferably from about 5 minutes to about 1 hour, and most preferably from 20 minutes to 50 minutes, and, optionally, include the presence of the above described initiator.

Now referring to the FIGURE, therein is depicted by schematic representation a specific embodiment of the present invention wherein liquid acid catalysts (HF and/or $H_2SO_4$) are used in the alkylation and disproportionation processes. The FIGURE is for illustration purposes only and is not intended to limit the invention as set out in the specification and the appended claims. An isoparaffin stream, preferably comprising isobutane, is charged to riser reactor 10 via conduit 12 and a recycle isoparaffin stream, preferably comprising isobutane, is charged to riser reactor 10 via conduits 14 and 12 wherein the isoparaffins are alkylated by olefins, preferably butenes, contained in an olefin stream charged to riser reactor 10 via conduit 16, in the presence of an alkylation catalyst charged to riser reactor 10 via conduit 18, thereby forming an alkylation reaction mixture. The alkylation reaction mixture is charged to alkylation unit settler 20 via conduit 22 and is combined with a disproportionation reaction mixture charged to alkylation unit settler 20 via conduit 24, thereby forming a combined mixture. The combined mixture in alkylation unit settler 20 is permitted to settle thereby forming a hydrocarbon phase 26 and a catalyst phase 28. The catalyst phase 28 can be removed via conduit 18 for use as the alkylation catalyst or can be sent downstream for further processing or for use as an acidic disproportionation catalyst via conduits 18 and 30. Hydrocarbon phase 26 is removed from alkylation unit settler 20 via conduit 32 and is charged to a separator 34 (which can be a fractionation tower or system) for separation. The recycle i-butane stream is removed from separator 34 via conduit 14, a n-butane/i-pentane mixture stream is removed from separator 34 via conduit 36, and a $C_5+$ alkylate stream is removed from separator 34 via conduit 38. The n-butane/i-pentane mixture stream is charged to a disproportionation reactor 40 via conduit 36 along with an initiator charged to disproportionation reactor 40 via conduits 42 and 36, and along with an acidic disproportionation catalyst charged to disproportionation reactor 40 via conduits 44 and 36, (and, optionally, conduit 30) thereby forming the disproportionation reaction mixture. The disproportionation reaction mixture is removed from disproportionation reactor 40 via conduit 24 and is charged to alkylation unit settler 20.

The following example demonstrates the advantages of the present invention. This example is for illustration purposes only and is not intended to limit the invention as set out in the specification and the appended claims.

EXAMPLE

This example illustrates the benefits of disproportionating i-pentane (i-$C_5$) in the presence of a lower paraffin (such as n-butane).

The disproportionation batch reactor was a monel autoclave of 300 ml capacity connected at one end to a monel sight gauge via ¼" monel tubing, and connected at the other end to a feed introduction line via ⅛" monel tubing.

For each run, the catalyst was circulated in the reactor at a stirring rate of 1500 rpm. The initial catalyst composition contained 94 wt. % HF, with the balance comprising dissolved light hydrocarbons and water.

Run 1 (Control)

For Run 1, a 47.1 gram quantity of a feed composition (presented in the table) was disproportionated in a batch reactor in which 142.5 grams of HF were stirred at 1500 rpm. The reactor temperature was about 199.4° F. and the volume to volume ratio of HF acid to hydrocarbon was about 2:1. The HF and disproportionation product were collected in a settler and allowed to separate. The disproportionation product was drawn off into a suitable sample cylinder, contacted with 8.5% KOH solution (to destroy free HF), collected, and analyzed by standard gas chromatography using a GC sample injection valve so that no light materials were lost. The separated disproportionation product was collected and analyzed at the end of the run (about 30 minutes). Test data results are provided in the Table.

Run 2 (Inventive)

For Run 2, a 46.9 gram quantity of a feed composition (presented in the table) was disproportionated in a batch reactor in which 146.7 grams of HF were stirred at 1500 rpm. The reactor temperature was about 197.8° F. and the volume to volume ratio of HF acid to hydrocarbon was about 2:1. The HF and disproportionation product were collected in a settler and allowed to separate. The disproportionation product was drawn off into a suitable sample cylinder, contacted with 8.5% KOH solution (to destroy free HF), collected, and analyzed by standard gas chromatography using a GC sample injection valve so that no light materials were lost. The separated disproportionation product was collected and analyzed at the end of the run (about 30 minutes). Test data results are provided in the Table.

Run 3 (Inventive)

For Run 3, a 46.8 gram quantity of a feed composition (presented in the Table) was disproportionated in a batch reactor in which 146.9 grams of HF were stirred at 1500 rpm. The reactor temperature was about 197.7° F. and the volume to volume ratio of HF acid to hydrocarbon was about 2:1. The HF and disproportionation product were collected in a settler and allowed to separate. The disproportionation product was drawn off into a suitable sample cylinder, contacted with 8.5% KOH solution (to destroy free HF), collected, and analyzed by standard gas chromatography using a GC sample injection valve so that no light materials were lost. The separated disproportionation product was collected and analyzed at the end of the run (about 30 minutes). Test data results are provided in the Table.

Run 4 (Inventive)

For Run 4, a 43.2 gram quantity of a feed composition (presented in the table) was disproportionated in a batch reactor in which 146.9 grams of HF were stirred at 1500 rpm. The reactor temperature was about 207.7° F. and the volume to volume ratio of HF acid to hydrocarbon was about 2:1. The HF and disproportionation product were collected in a settler and allowed to separate. The disproportionation product was drawn off into a suitable sample cylinder, contacted with 8.5% KOH solution (to destroy free HF), collected, and analyzed by standard gas chromatography using a GC sample injection valve so that no light materials were lost. The separated disproportionation product was collected and analyzed at the end of the run (about 30 minutes). Test data results are provided in the Table.

Run 5 (Inventive)

For Run 5, a 44.0 gram quantity of a feed composition (presented in the table) was disproportionated in a batch reactor in which 144.5 grams of HF were stirred at 1500 rpm. The reactor temperature was about 195.8° F. and the volume to volume ratio of HF acid to hydrocarbon was about 2:1. The HF and disproportionation product were collected in a settler and allowed to separate. The disproportionation product was drawn off into a suitable sample cylinder, contacted with 8.5% KOH solution (to destroy free HF), collected, and analyzed by standard gas chromatography using a GC sample injection valve so that no light materials were lost. The separated disproportionation product was collected and analyzed at the end of the run (about 30 minutes). Test data results are provided in the Table.

Run 6 (Inventive)

For Run 6, a 44.3 gram quantity of a feed composition (presented in the table) was disproportionated in a batch reactor in which 147.3 grams of HF were stirred at 1500 rpm. The reactor temperature was about 192.9° F. and the volume to volume ratio of HF acid to hydrocarbon was about 2:1. The HF and disproportionation product were collected in a settler and allowed to separate. The disproportionation product was drawn off into a suitable sample cylinder, contacted with 8.5% KOH solution (to destroy free HF), collected, and analyzed by standard gas chromatography using a GC sample injection valve so that no light materials were lost. The separated disproportionation product was collected and analyzed at the end of the run (about 30 minutes). Test data results are provided in the Table.

Run 7 (Inventive)

For Run 7, a 44.9 gram quantity of a feed composition (presented in the table) was disproportionated in a batch reactor in which 144.0 grams of HF were stirred at 1500 rpm. The reactor temperature was about 191.7° F. and the volume to volume ratio of HF acid to hydrocarbon was about 2:1. The HF and disproportionation product were collected in a settler and allowed to separate. The disproportionation product was drawn off into a suitable sample cylinder, contacted with 8.5% KOH solution (to destroy free HF), collected, and analyzed by standard gas chromatography using a GC sample injection valve so that no light materials were lost. The separated disproportionation product was collected and analyzed at the end of the run (about 30 minutes). Test data results are provided in the Table.

TABLE

| Run | $i\text{-}C_5^1$ wt. % in feed | $i\text{-}C_4$ wt. % in feed | $i\text{-}C_5$ conv., wt. % | $n\text{-}C_4$ conv., wt. % | $i\text{-}C_4$ select[2] | $C_6+$ select[3] |
|---|---|---|---|---|---|---|
| 1 | 98.64 | — | 47.77 | — | 30.9 | 67.8 |
| 2 | 93.56 | 5.69 | 65.56 | 5.52 | 37.1 | 60.8 |
| 3 | 88.83 | 10.48 | 67.22 | 9.04 | 36.4 | 60.1 |
| 4 | 74.65 | 24.74 | 69.55 | 14.75 | 41.7 | 54.5 |
| 5 | 49.92 | 49.64 | 64.77 | 12.35 | 42.2 | 54.2 |
| 6 | 25.69 | 74.04 | 60.94 | 10.90 | 54.1 | 42.0 |
| 7 | 11.05 | 88.78 | 53.53 | 7.59 | 66.0 | 30.0 |

[1]includes $i\text{-}C_5$ paraffin and less than 2 wt. % $i\text{-}C_5$ olefin.
[2]$i\text{-}C_4$ selectivity = (g of $i\text{-}C_4$ in product − g of $i\text{-}C_4$ in feed)/(g of $i\text{-}C_5$ converted + g of $n\text{-}C_4$ converted).
[3]$C_6+$ selectivity = (g of $C_6+$ in product − g of $C_6+$ in feed)/(g of $i\text{-}C_5$ converted + g of $n\text{-}C_4$ converted).

The test data presented in the Table show that the inventive process of disproportionating $i\text{-}C_5$ in the presence of a $n\text{-}C_4$ co-feed (Inventive Runs 214 7) results in increased conversion of $i\text{-}C_5$ and increased $i\text{-}C_4$ selectivity as compared to Control Run 1 wherein $i\text{-}C_5$ is disproportionated without a $n\text{-}C_4$ co-feed.

Inventive Runs 2–7 demonstrated increased $i\text{-}C_5$ conversions ranging from 53.53 wt. % to 69.55 wt. % as compared to the $i\text{-}C_5$ conversion in Control Run 1 of only 47.77 wt. %.

Also, Inventive Runs 2–7 demonstrated increased $i\text{-}C_4$ selectivities ranging from 36.4 to 66.0 as compared to the $i\text{-}C_4$ selectivity in Control Run 1 of only 30.9.

The $i\text{-}C_4$ produced can be used as a feed to an $i\text{-}C_4$ alkylation process to produce alkylate, and the $C_6+$ material can be blended into gasoline or sent downstream for further processing.

Reasonable variations, modifications, and adaptations can be made within the scope of the disclosure and the appended claims without departing from the scope of this invention.

That which is claimed is:

1. A process for disproportionating isopentane comprising contacting a hydrocarbon feed comprising at least one isopentane and a lower paraffin comprising a hydrocarbon selected from the group consisting of propane, n-butane, and combinations thereof, with an acidic disproportionation catalyst in a reaction zone under disproportionation reaction conditions; wherein the mole ratio of said at least one isopentane to said lower paraffin in said hydrocarbon feed is in the range of from about 0.01 to about 80.

2. A process in accordance with claim 1 wherein said disproportionation reaction conditions include the presence of an initiator.

3. A process in accordance with claim 2 wherein the concentration of said initiator in said reaction zone, based on the combined weight of said hydrocarbon feed and said initiator in said reaction zone, is greater than about 0.01 wt. %.

4. A process in accordance with claim 2 wherein said initiator comprises a compound selected from the group consisting of a haloalkane, a branched paraffin, at least one olefin, and combinations of any two or more thereof.

5. A process in accordance with claim 4 wherein said haloalkane comprises a compound selected from the group consisting of fluoropropane, fluorobutanes, fluoropentanes, and combinations of any two or more thereof.

6. A process in accordance with claim 4 wherein said branched paraffin comprises a multi-branched paraffin having in the range of from 4 to 20 carbon atoms per molecule, and combinations of any two or more thereof.

7. A process in accordance with claim 4 wherein said at least one olefin comprises an olefin having in the range of from 3 to 20 carbon atoms per molecule, and combinations of any two or more thereof.

8. A process in accordance with claim 4 wherein said at least one olefin comprises a mixture of propylene, a butylene and a pentene.

9. A process in accordance with claim 1 wherein said disproportionation reaction conditions include a temperature in the range of from about 75° F. to about 375° F.

10. A process in accordance with claim 1 wherein said acidic disproportionation catalyst is suitable for catalyzing a hydrogen transfer reaction between secondary and tertiary carbenium ions.

11. A process in accordance with claim 1 wherein said acidic disproportionation catalyst comprises an acid selected from the group consisting of sulfuric acid, hydrofluoric acid, and a polyfluoroalkane sulfonic acid, wherein the polyfluoroalkane moiety contains in the range of from 1 to 20 carbon atoms.

12. A process in accordance with claim 1 wherein said acidic disproportionation catalyst is hydrofluoric acid.

13. A process in accordance with claim 1 wherein said disproportionation reaction conditions include a contact time of said hydrocarbon feed with said acidic disproportionation catalyst in the range of from about 30 seconds to about 2 hours.

14. A process in accordance with claim 1 wherein said hydrocarbon feed is further characterized to comprise less than 6 wt. % water.

15. A process for upgrading an alkylation reaction product comprising the steps of:
   alkylating an isoparaffin with an olefin in the presence of an alkylation catalyst to thereby form an alkylation reaction mixture comprising an alkylation reaction product and said alkylation catalyst;
   combining said alkylation reaction mixture with a disproportionation reaction mixture comprising a disproportionation reaction product and an acidic disproportionation catalyst to thereby form a combined mixture;
   separating a hydrocarbon phase from said combined mixture;
   separating said hydrocarbon phase into at least a n-butane/i-pentane mixture stream comprising n-butane and i-pentane;
   charging said n-butane/i-pentane mixture stream to a disproportionation reaction zone for contact, under disproportionation reaction conditions, with said acidic disproportionation catalyst to thereby form said disproportionation reaction mixture.

16. A process in accordance with claim 15 wherein said disproportionation reaction conditions include the presence of an initiator.

17. A process in accordance with claim 16 wherein the concentration of said initiator in said disproportionation reaction zone, based on the combined weight of said n-butane/i-pentane mixture stream and said initiator in said disproportionation reaction zone, is greater than about 0.01 wt. %.

18. A process in accordance with claim 16 wherein said initiator comprises a compound selected from the group consisting of a haloalkane, a branched paraffin, at least one olefin, and combinations of any two or more thereof.

19. A process in accordance with claim 18 wherein said haloalkane comprises a compound selected from the group consisting of fluoropropane, fluorobutanes, fluoropentanes, and combinations of any two or more thereof.

20. A process in accordance with claim 18 wherein said branched paraffin comprises a multi-branched paraffin having in the range of from 4 to 20 carbon atoms per molecule.

21. A process in accordance with claim 18 wherein said at least one olefin comprises an olefin having in the range of from 3 to 20 carbon atoms per molecule, and combinations of any two or more thereof.

22. A process in accordance with claim 18 wherein said at least one olefin comprises a mixture of propylene, butylene and pentene.

23. A process in accordance with claim 15 wherein the mole ratio of i-pentane to n-butane in said n-butane/i-pentane mixture stream is in the range of from about 0.01 to about 80.

24. A process in accordance with claim 15 wherein said disproportionation reaction conditions include a temperature in the range of from about 75° F. to about 375° F.

25. A process in accordance with claim 15 wherein said acidic disproportionation catalyst is suitable for catalyzing a hydrogen transfer reaction between secondary and tertiary carbenium ions.

26. A process in accordance with claim 15 wherein said acidic disproportionation catalyst comprises an acid selected from the group consisting of sulfuric acid, hydrofluoric acid, and polyfluoroalkane sulfonic acids, wherein the alkane moiety contains in the range of from 1 to 20 carbon atoms.

27. A process in accordance with claim 15 wherein said acidic disproportionation catalyst is hydrofluoric acid.

28. A process in accordance with claim 15 wherein said disproportionation reaction conditions include a contact time of said n-butane/i-pentane mixture stream with said acidic disproportionation catalyst in the range of from about 30 seconds to about 2 hours.

29. A process in accordance with claim 15 wherein said n-butane/i-pentane mixture stream is further characterized to comprise less than 6 wt. % water.

30. A process in accordance with claim 15 wherein said hydrocarbon phase is further separated into an i-butane stream comprising i-butane and a $C_5+$ alkylate stream comprising hydrocarbons having greater than 4 carbon atoms per molecule.

* * * * *